US011389387B2

(12) United States Patent
Haake et al.

(10) Patent No.: US 11,389,387 B2
(45) Date of Patent: Jul. 19, 2022

(54) PROTEIN HYDROLYSATES

(71) Applicant: BASF SE, Ludwigshafen am Rhein (DE)

(72) Inventors: Hans-Martin Haake, Düsseldorf-Holthausen (DE); Christina Kohlmann, Monheim (DE); Christian Markiefka, Monheim (DE); Guadalupe Pellon, Monheim (DE); Ansgar Behler, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/332,230

(22) PCT Filed: Sep. 5, 2017

(86) PCT No.: PCT/EP2017/072217
§ 371 (c)(1),
(2) Date: Mar. 11, 2019

(87) PCT Pub. No.: WO2018/068947
PCT Pub. Date: Apr. 19, 2018

(65) Prior Publication Data
US 2019/0216709 A1 Jul. 18, 2019

(30) Foreign Application Priority Data
Sep. 13, 2016 (EP) .................................... 16188517

(51) Int. Cl.
*A61K 8/64* (2006.01)
*A61Q 5/12* (2006.01)
*A61K 8/66* (2006.01)

(52) U.S. Cl.
CPC ............... *A61K 8/645* (2013.01); *A61K 8/66* (2013.01); *A61Q 5/12* (2013.01); *A61K 2800/805* (2013.01)

(58) Field of Classification Search
CPC .... A61K 8/645; A61K 8/66; A61K 2800/805; A61Q 5/12
See application file for complete search history.

(56) References Cited

U.S. PATENT DOCUMENTS

| 2,457,820 A * | 1/1949 | Howe ................... A61K 31/16 514/400 |
| 6,013,250 A | 1/2000 | Cannell et al. |
| 6,509,011 B1 | 1/2003 | Ellis et al. |
| 2004/0067279 A1* | 4/2004 | Delest ...................... C12C 5/00 426/42 |

FOREIGN PATENT DOCUMENTS

| CN | 1254276 A | 5/2000 | |
| CN | 1374851 A | 10/2002 | |
| EP | 2384124 A1 | 11/2011 | |
| JP | S62-53909 A | 3/1987 | |
| JP | H07-242531 A | 9/1995 | |
| JP | H09-278630 A | 10/1997 | |
| JP | 2006-137755 A | 6/2006 | |
| JP | 2007-295920 A | 11/2007 | |
| WO | WO-96/25141 A1 | 8/1996 | |
| WO | WO-2010/029007 A2 | 3/2010 | |
| WO | WO-2010029007 A2 * | 3/2010 | ............... A61K 8/44 |
| WO | WO-2018/10869 A1 | 1/2018 | |

OTHER PUBLICATIONS

WO2010/029007 Machine Translation of document (Year: 2010).*
Enrique Yanez, et al., Enzymatic Fish Protein Hydrolyzate: Chemical Composition, Nutritive Value and Use as a Supplement to Cereal Protein, 41 J Food Sci. 1289 (Year: 1976).*
European Patent Application No. 16188517.3, European Search Report, dated Jan. 2, 2017, 3 pages.
International Application No. PCT/EP2017/072217, International Preliminary Report on Patentability, dated Mar. 19, 2019.
International Application No. PCT/EP2017/072217, International Search Report and Written Opinion, dated May 30, 2018.
Mitsuda, et al., "Studies on protein foods (Part 7): Protein isolate from rice bran and its nutritive value", Journal of Japanese Society of Food and Nutrition, vol. 23, Issue 2, 1969, pp. 80-84.
Google Patent translation of WO2010/029007 dated Aug. 23, 2021.
Decision to Grant a Patent in Japanese Patent Application No. 2019-513812 dated Dec. 7, 2021.
Written Amendment in Japanese Patent Application No. 2019-513812 dated Oct. 6, 2021.
Written Opinion in Japanese Patent Application No. 2019-513812 dated Oct. 6, 2021.
Notice of Reasons for Refusal in Japanese Patent Application No. 2019-513812 dated Jul. 6, 2021.

* cited by examiner

*Primary Examiner* — Sean M Basquill
(74) *Attorney, Agent, or Firm* — Marshall, Gerstein & Borun LLP

(57) ABSTRACT

The subject of the application is protein hydrolyzates having specific amounts of the amino acids arginine and lysine, which demonstrate improved properties in hair treatment compositions and in cleansing compositions for skin and hair, and also enzymatic methods for the preparation thereof, and the cosmetic compositions comprising same.

11 Claims, No Drawings

PROTEIN HYDROLYSATES

This application is a National Stage application of International Application No. PCT/EP2017/072217, filed Sep. 5, 2017, which claims the benefit of European Patent Application No. 16188517.3, filed on Sep. 13, 2016.

FIELD OF THE INVENTION

The invention relates to the field of cosmetics and concerns protein hydrolyzates having selected compositions of amino acids, methods for the preparation thereof and the use thereof in cosmetic compositions and also the cosmetic compositions.

PRIOR ART

Proteins, and especially keratin, are important ingredients for the cosmetics industry. Because of their film-forming properties, proteins may form a protective layer on skin and hair and thereby care for them. Proteins have many other advantages and are therefore widely used in a wide variety of different cosmetic compositions for skin and hair, with keratin being predominantly used in haircare.

Because of their poor solubility, however, proteins are not usually used in their natural form in cosmetic formulations but rather as what are referred to as "hydrolyzates". In hydrolysis, the peptide bridges within a protein are cleaved by the action of strong acids, bases or catalysts and protein hydrolyzates are obtained, that is to say mixtures of smaller protein fragments, peptides and in some cases even amino acids. Depending on the type of preparation method, the protein hydrolyzates contain other protein fragments. Since chemical hydrolysis using acids or bases occurs in a non-specific manner and also commonly leads to products with poorer quality, especially in terms of color, odor and stability, enzymatic hydrolysis of proteins is the preferred method, particularly for cosmetic applications. In contrast to chemical hydrolysis, enzymatic hydrolysis occurs under moderate reaction conditions in terms of pH, temperature and pressure. Furthermore, the enzymes used are known for their specificity; i.e., in contrast to chemical hydrolysis the composition of the resultant protein hydrolyzates is more uniform and thus leads to consistent product compositions.

International patent application WO 96/25141 A1 describes cationized plant-based protein surfactants which are firstly hydrolyzed at a pH in the range from 8 to 10 with proteinases and optionally subsequently hydrolyzed at a pH in the range from 6-7 with (exo)peptidases.

International patent application WO 2008/115165 A2 describes highly specifically hydrolyzed rice proteins, with enzymatic hydrolysis occurring firstly with the endoprotease Alcalase® in the alkaline range at a pH of 7.5 to 8 and subsequently with a protease such as Flavorzyme® at pH 6.5. This is followed by a further hydrolysis with the Dual Protease Enzyme® and Neutrase (Novo), before filtration takes place with a membrane filter. The retentate has an average molecular weight of 3500 and the permeate has an average molecular weight of 200.

In the cosmetic use examples, the cited application discloses rice hydrolyzates which have subsequently been further cationically modified, or had hydrolyzed rice starch added thereto.

International patent application WO 2009/155557 discloses protein hydrolyzate mixtures having a mixture of oligopeptides having an average molecular weight of less than 10 000 Daltons, a degree of hydrolysis of at least 2.5% and a "solid solubility index" of at least 60%. These protein hydrolyzate mixtures may be derived from animal and plant proteins, and especially from soy. The oligopeptides are obtained by bringing the protein material into contact with at least one endopeptidase, that is to say by means of enzymatic hydrolysis. A mixture of soy and rice is proposed as protein material, without a ratio being stated. The application of the disclosed hydrolyzate mixtures is exclusively in the field of nutrition.

European patent application EP 2384124 B1 also describes protein hydrolyzates, for example based on rice or soy, which are prepared by enzymatic hydrolysis using an endopeptidase, with the 47 kDa fragment accounting for approximately 10 to 66% of the polypeptides.

In cosmetics, predominantly keratin hydrolyzates have hitherto been used as protein hydrolyzates, since they are able to be adsorbed on the surface of the hair and thus contribute to giving the hair more body. The hair cuticle appears smoother, and the hair appears healthier and more shiny. In other words, the hair's protective layer is externally strengthened.

The object of the present invention was to provide protein hydrolyzates, the implementation of which in haircare products is comparable in terms of performace to that of keratin hydrolyzates. Furthermore, the protein hydrolyzates should lead to strengthening of the hair from the inside, that is to say to improving the internal hair structure. The hair should remain more elastic, and hair that is already damaged should be regenerated or repaired from the inside, such that higher elasticity is obtained (or regained). In addition, the protein hydrolyzates should demonstrate a very good conditioning effect. Hair conditioning is understood by those skilled in the art to mean the treatment of hair with caring "rinse-off" formulations (i.e. formulations which are rinsed off) or "leave-on" formulations (i.e. formulations which remain on the hair without being rinsed off), especially with caring shampoos or conditioners. This treatment leads especially to easier combability of the hair in the wet and dry state, both along the lengths and at the tips (better detanglability), to improved tactile properties such as smoothness, softness and suppleness and also to more hair shine, less electrostatic charge and improved ease of styling. On the whole, a cared-for and healthy overall condition of the hair is thus achieved by the conditioning.

Finally, the protein hydrolyzates should be easy to prepare, highly storage-stable without thickening and able to be readily formulated in hair and skin treatment compositions.

The object was solved by a protein hydrolyzate consisting of free and peptide-bound amino acids, wherein 8.0-25 wt % of the amino acids are arginine and 4.5-25 wt % of the amino acids are lysine.

Further subjects of the present invention are a method for preparing a corresponding protein hydrolyzate 1, wherein a mixture of soy and rice proteins in a weight ratio of 2:1 to 4:1 is enzymatically hydrolyzed in the presence of at least one endopeptidase.

Further subjects of the present invention are the use of the inventive protein hydrolyzates for improving at least one of the properties in hair treatment compositions:
protecting against environmental influences that damage the hair
repairing damaged hair
tensile strength of human hair
stabilizing the moisture balance of human hair
combability of human hair
breakage of human hair
restructurability of human hair
reducing the loss of elasticity of human hair.

The use of the inventive protein hydrolyzates as conditioner and also for improving the internal hair structure in hair treatment compositions are also subjects of the present invention, as is the use of the inventive protein hydrolyzates for improving the sensory feel in cosmetic compositions for cleansing skin and/or hair, preferably the sensory feel of foam and especially in body washes or shower gels.

In the context of the present invention, the term "protein hydrolyzate" is defined as a mixture of fragments obtained from the hydrolytic degradation of proteins. Such mixtures comprise free amino acids and peptide-bound amino acids with different molecular weights and compositions.

In the context of the invention, the amino acid composition was determined according to ISO 13903:2005, which determines the proportion of free amino acids and the total amino acids. Differentiation between D- and L-forms of the amino acids does not occur.

In the scope of the invention, the molecular weight is defined in Daltons (Da) and the molecular weight distribution is determined by liquid chromatography.

In order to determine the molecular weight distribution, the liquid chromatography apparatus Agilent 1260 Infinity with binary pump and degasser was used in combination with PSS WinGPC UniCh-rom. PSS WinGPC UniChrom is a macromolecular chromatography data system with manufacturer-independent real-time data acquisition for comprehensive analysis of macromolecules, and is particularly suitable for the analysis of polymers, biopolymers and proteins.

The chromatographic column used is a specific chromatographic column (Superdex Peptide 10/300 GL from GE Healthcare Life Science, pore width 100 Å, 5 µm particle size) for high-resolution separation of proteins and peptides. This column was chosen because it is particularly well-suited to determine biomolecules with molecular weights between 100 and 7000. Dilute hydrochloric acid (0.05 M) with a flow rate of 0.5 ml/min was used as eluent. Detection was carried out with a diode array detector (DAD) at 214 nm.

In the context of the present invention, the amino group of the amino acids may be present free, protonated or derivatized and the carboxyl group of the amino acid may be present free, deprotonated or derivatized in the protein hydrolyzate.

The proportion of the amino acids arginine and lysine in the protein hydrolyzate is essential in the context of the invention. Preferably, 5.0 to 25 wt %, especially 6.0 to 25 wt % of the amino acids are lysine. Preferably, 8.2 to 25 wt % of the amino acids are arginine. Protein hydrolyzates, wherein 8.2 to 8.5 wt % of the amino acids are arginine and 6.0 to 6.5 wt % of the amino acids are lysine, are especially suitable.

These proportions (wt %) of arginine and lysine are different from protein hydrolyzates known to date. Thus, keratin hydrolyzates have 9.3% arginine and 2.5% lysine, wheat hydrolyzates have 3.1% arginine and 1.4% lysine, soy hydrolyzates have 7.8% arginine and 6.2% lysine and rice hydrolyzates have 7.91% arginine and 5.77% lysine.

In the scope of the invention, it was possible to demonstrate that the inventive amounts of amino acids in the protein hydrolyzates demonstrate significantly better properties when used in hair treatment compositions and in cleansing compositions for skin and hair than protein hydrolyzates based on the abovementioned protein hydrolyzates.

The inventive protein hydrolyzates can be prepared from a soy and rice mixture in the weight ratio of 2.0:1 to 3.5:1, preferably 2.5:1 to 3.5:1 and especially 3:1.

Soy in the form of soy flour, soy flakes, soy milk, soy milk powder, soy protein powder and/or soy protein concentrate, especially soy protein powder, can be used as starting material.

Rice in the form of rice flour, rice protein powder and/or rice protein concentrate, especially rice protein powder, can be used as starting material.

In the context of the invention, it is advantageous if the mixture of soy and rice proteins jointly is enzymatically hydrolyzed.

According to one embodiment, the inventive soy and rice hydrolyzates are prepared by a single-stage enzymatic hydrolysis. Enzymatic hydrolysis is carried out using an endopeptidase, preferably at an alkaline pH in the range from 8 to 9. The endopeptidases are preferably selected from *Bacillus* strains, especially *Bacillus licheniformis, Bacillus alcaophilus, Bacillus subtilis, Bacillus mesentericus* or *Bacillus firmus*. Those endopeptidases from *Bacillus licheniformis* that are commercially available for example as Alcalase® from Novozymes are especially suitable.

According to a further embodiment, the inventive soy and rice hydrolyzates are prepared by enzymatic hydrolysis performed twice, with the first enzymatic hydrolysis already described above being followed by a further enzymatic hydrolysis in the presence of an exopeptidase, preferably at a neutral pH of 6.5 to 7.5. Exopeptidases include alpha-amino acyl peptide hydrolases (EC 3.4.11), which detach individual amino acids at the end of the polypeptide, dipeptide hydrolases or dipeptidases (EC 3.4.13), which hydrolyze dipeptides to give amino acids, dipeptidyl peptide hydrolases or dipeptidyl peptidases (EC 3.4.14), which release amino-constant dipeptides of a polypeptide, peptidyl dipeptide hydrolases or dipeptidyl carboxypeptidases (EC 3.4.15), which separate off individual amino acids from the carboxyl terminus, carboxypeptidases (EC 3.4.16 3.4.18) and omega peptidases (EC 3.4.19), which cleave modified amino acids from both ends of the polypeptide. Special preference is given to those obtainable from *Aspergillus oryzae*, such as the commercially available Flavourzyme® from Novozymes.

The enzymatic hydrolyses preferably take place until completion, which can be determined by those skilled in the art in a known manner, for example by determining the constant pH or by means of size exclusion chromatography or photometrically using detection of free $NH_2$ groups.

The amount of endopeptidases and/or exopeptidases used is not critical per se, but should be in the range from 0.05 to 5, preferably 0.1 to 2 wt % based on protein-containing starting material.

The hydrolyzates obtained may finally be worked up, for example by filtering off undissolved fractions. For better stabilization, the pH is preferably set to values between 3.5 and 5.

The hydrolyzates obtained are aqueous solutions and may be used directly or in concentrated form; they preferably have a solids content in the range from 10 to 50 wt %, preferably 15 to 30 wt %. However, it is also possible to produce the protein hydrolyzates as powder by dewatering.

The protein hydrolyzates obtained after the enzymatic hydrolysis performed twice have a low molecular weight. They have an average molecular weight in the range from 800 to 3000 Da, preferably 1000 to 2500 and especially around 1400 Da.

According to a further embodiment of the invention, the inventive protein hydrolyzates are used for improving at least one of the properties in hair treatment compositions:

protecting against environmental influences that damage the hair
repairing damaged hair
tensile strength of human hair
stabilizing the moisture balance of human hair
combability of human hair
breakage of human hair
restructurability of human hair
reducing the loss of elasticity of human hair.

The use for improving the tensile strength of human hair, reducing the loss of elasticity of human hair and also significantly less hair breakage, are particularly advantageous.

Hair treatment compositions are understood to mean all cosmetic hair treatment compositions intended for cleansing, caring for, drying, or changing the color or changing the structure of the hair. For example, this is intended to include hair shampoos, hair conditioners, conditioning shampoos, hairsprays, hair rinses, hair treatments, hair masks, hair tonics, permanent wave fixing solutions, hair coloring shampoos, hair colorants, hair setting compositions, hair arranging compositions, hairstyling preparations, blowdrying lotions, mousses, hair gels, hair waxes or combinations thereof.

The inventive protein hydrolyzates may be used according to the invention as conditioners in hair treatment compositions, especially in caring hair shampoos, hair conditioners, conditioning shampoos, hair rinses, hair treatments, hair masks, hair serums, hair tonics, hair setting compositions, hairstyling preparations, mousses, hair gels and/or hair waxes.

The hair treatment compositions typically contain further ingredients such as surfactants, emulsifiers, cosurfactants, (cationic) polymers, oil bodies, emulsifiers, pearlizing waxes, consistency regulators, thickeners, superfatting agents, stabilizers, silicone compounds, fats, waxes, lecithins, phospholipids, UV light protection factors, biogenic active ingredients, antioxidants, antidandruff agents, film formers, swelling agents, tyrosine inhibitors (depigmenting agents), hydrotropes, solubilizers, preservatives, perfume oils, dyes and the like.

A further subject of the present invention relates to the use of the inventive protein hydrolyzates for improving the sensory feel in cosmetic compositions for cleansing skin and/or hair, preferably the sensory feel of foam and especially in body washes or shower gels.

The cosmetic compositions for cleansing skin and/or hair typically contain, as further ingredients, the ingredients already listed under hair treatment compositions, such as surfactants, emulsifiers, cosurfactants, (cationic) polymers, oil bodies, emulsifiers, pearlizing waxes, consistency regulators, thickeners, superfatting agents, stabilizers, fats, waxes, lecithins, phospholipids, biogenic active ingredients, antioxidants, antidandruff agents, film formers, (swelling agents), hydrotropes, solubilizers, preservatives, perfume oils, dyes and the like.

The inventive protein hydrolyzates are present in the cosmetic compositions in amounts of 0.002 to 0.4, preferably in amounts of 0.001 to 0.4 wt % based on the active substance content, or in amounts of 0.01 to 2 wt % based on a 20 wt % formulation of protein hydrolyzate in water.

Suitable further ingredients for the inventive use in the cosmetic compositions are listed below.

Surfactants

Surface-active substances may include anionic, nonionic, cationic, amphoteric or zwitterionic surfactants, the proportion of which in the compositions is customarily approximately 1 to 70, preferably 5 to 50 and especially 10 to 30 wt %. Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (especially wheat-based plant products) and alkyl (ether) phosphates. If the anionic surfactants comprise polyglycol ether chains, these may have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, partially oxidized alk(en)yl oligoglycosides and glucuronic acid derivatives, fatty acid N-alkylglucamides, polyol fatty acid esters, sugar esters, sorbitan esters, polysorbates and amine oxides. If the nonionic surfactants comprise polyglycol ether chains, these may have a conventional homolog distribution, but preferably have a narrowed homolog distribution. Typical examples of cationic surfactants are quaternary ammonium compounds, such as, for example, dimethyldistearylammonium chloride are especially quaternary ammonium compounds usable. Preference is given to ammonium halides, especially chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Furthermore, the very readily biodegradable quaternary ester compounds, such as, for example, the dialkylammonium methosulfates and methylhydroxyalkyldialkoyloxy-alkylammonium methosulfates sold under the trade name Stepantex® and the corresponding products of the Dehyquart® series can be used as cationic surfactants. The term "ester quats" is generally understood to mean quaternized fatty acid triethanolamine ester salts. Products that are commercially available as Dehyquart® L80, Dehyquart® F 75, Dehyquart® A-CA, are particularly preferred as cationic surfactants.

Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, fatty acid glucamides, and/or protein fatty acid condensates. Typical examples of amphoteric or zwitterionic surfactants are alkyl betaines, alkyl amido betaines, aminopropionates, aminoglycinates, imidazolinium betaines and sulfobetaines. The surfactants mentioned are exclusively known compounds.

Among the nonionic surfactants, preference is given, especially for cosmetic skin treatment compositions such as shower gels and body washes, to alkyl and alkenyl oligoglycosides corresponding to the formula $$RO-[G]_p$$

in which R is an alkyl and/or alkenyl radical having 4 to 22 carbon atoms, G is a sugar radical having 5 or 6 carbon atoms and p is numbers from 1 to 10. They can be obtained by the relevant methods of preparative organic chemistry. The alkyl and/or alkenyl oligoglycosides can be derived from aldoses or ketoses having 5 or 6 carbon atoms, preferably from glucose. The preferred alkyl and/or alkenyl oligoglycosides are therefore alkyl and/or alkenyl oligoglucosides. The index number p specifies the degree of oligomerization (DP), i.e. the distribution of mono- and oligoglycosides and is a number between 1 and 10. Whereas p in a given compound must always be an integer and can here in particular assume the values p=1 to 6, the value p for a particular alkyl oligoglycoside is an analytically determined calculated parameter which in most cases is a fraction. Preference is given to using alkyl and/or alkenyl oligoglycosides having a mean degree of oligomerization p of 1.1 to 3.0. From a technical applications perspective, preference is given to those alkyl and/or alkenyl oligoglycosides for which the degree of oligomerization is less than 1.7 and is especially between 1.2 and 1.4.

The alkyl or alkenyl radical R can be derived from primary alcohols having 4 to 11, preferably 8 to 10 carbon atoms. Typical examples are butanol, caproic alcohol, caprylic alcohol, capric alcohol and undecyl alcohol, and also their technical-grade mixtures, as obtained, for example, in the hydrogenation of technical-grade fatty acid methyl esters or during the hydrogenation of aldehydes from Roelen's oxo synthesis. Preference is given to alkyl oligoglucosides having a chain length of C8-C10 (DP=1 to 3), which are obtained as forerun in the distillative separation of technical-grade C8-C18-coconut fatty alcohol, and may be contaminated with a fraction of less than 6 wt % of C12-alcohol and also alkyl oligoglucosides based on technical-grade C9/11-oxo alcohols (DP=1 to 3). The alkyl or alkenyl radical R can further also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and also the technical-grade mixtures thereof which may be obtained as described above. Preference is given to alkyl oligoglucosides based on hardened C12/14-coconut alcohol with a DP of 1 to 3.

Suitable amphoteric or zwitterionic surfactants are alkyl betaines, alkylamido betaines, aminopropionates, aminoglycinates, imidazolinium betaines and sulfobetaines. Examples of suitable alkyl betaines are the carboxyalkylation products of secondary and especially tertiary amines. Typical examples are the carboxymethylation products of hexylmethylamine, hexyldimethylamine, octyldimethylamine, decyldimethylamine, dodecylmethylamine, dodecyldimethylamine, dodecylethylmethylamine, C12/14-cocoalkyldimethylamine, myristyldimethylamine, cetyldimethylamine, stearyldimethylamine, stearylethylmethylamine, oleyldimethylamine, C16/18-tallowalkyldimethylamine and also the technical-grade mixtures thereof. Furthermore, carboxyalkylation products of amidoamines are also included. Typical examples are reaction products of fatty acids having 6 to 22 carbon atoms, namely caproic acid, caprylic acid, capric acid, lauric acid, myristic acid, palmitic acid, palm oleic acid, stearic acid, isostearic acid, oleic acid, elaidic acid, petroselinic acid, linoleic acid, linolenic acid, elaeostearic acid, arachidic acid, gadoleic acid, behenic acid and erucic acid and also the technical-grade mixtures thereof, with N,N-dimethylaminoethylamine, N,N-dimethylaminopropylamine, N,N-diethylaminoethylamine and N,N-diethylaminopropylamine, which are condensed with sodium chloroacetate. Preference is given to the use of a condensation product of C8/18-coconut fatty acid-N,N-dimethylaminopropylamide with sodium chloroacetate.

Furthermore, imidazolinium betaines are also included. These substances are also known substances which can be obtained for example by cyclizing condensation of 1 or 2 mol of fatty acid with polyfunctional amines such as, for example, aminoethylethanolamine (AEEA) or diethylenetriamine. The corresponding carboxyalkylation products are mixtures of different open-chain betaines. Typical examples are condensation products of the abovementioned fatty acids with AEEA, preferably imidazolines based on lauric acid or again C12/14-coconut fatty acids which are subsequently betainized with sodium chloroacetate.

Oil Bodies

Useful oil bodies are, for example, Guerbet alcohols based on fatty alcohols having 6 to 18, preferably 8 to 10, carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of linear $C_6$-$C_{22}$ fatty acids with branched alcohols, especially 2-ethylhexanol, esters of $C_{18}$-$C_{38}$ alkylhydroxycarboxylic acids with linear or branched $C_6$-$C_{22}$ fatty alcohols, especially dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$ alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclic dimethicones, referred to as (INCI) Cyclomethicone, polymethylsiloxanes, referred to as (INCI) Dimethicone, amino-functional silicones, referred to as (INCI) Amodimethicone and Trimethylsilylamodimethicone, among others) and/or aliphatic or naphthenic hydrocarbons, such as, for example, squalane, squalene or dialkylcyclohexanes. Suitable silicone oils are described in European patent EP1830798 on pages 8-14, to which reference is hereby expressly made.

Emulsifiers

Suitable emulsifiers are, for example, nonionogenic surfactants from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl radical;

addition products of from 1 to 15 mol of ethylene oxide onto castor oil and/or hydrogenated castor oil;

addition products of from 15 to 60 mol of ethylene oxide onto castor oil and/or hydrogenated castor oil;

adducts having 1 to 30 mol of ethylene oxide onto partial esters of glycerol and/or sorbitan with unsaturated, linear or saturated, branched fatty acids having 12 to 22 carbon atoms and/or hydroxycarboxylic acids having 3 to 18 carbon atoms;

partial esters of polyglycerol (average degree of self-condensation 2 to 8), polyethylene glycol (molecular weight 400 to 5000), sorbitan, trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof having 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol.

mono-, di- and trialkyl phosphates, and mono-, di- and/or tri-PEG-alkyl phosphates and salts thereof;

wool wax alcohols;

polysiloxane-polyalkyl-polyether copolymers and corresponding derivatives;

block copolymers, for example polyethyleneglycol-30 dipolyhydroxystearates;

polymer emulsifiers, for example Pemulen grades (TR-1, TR-2) from Goodrich;

polyalkylene glycols and glycerol carbonate.

Particularly preferred emulsifiers are addition products of ethylene oxide onto 012/18-fatty acid mono- and diesters, addition products of 1 to 30, preferably 5 to 10 mol of ethylene oxide onto hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, maleic acid monoglyceride, maleic acid diglyceride, and the technical-grade mixtures thereof. Addition products of 1 to 30 mol, preferably 5 to 10 mol, of ethylene oxide onto sorbitan esters are likewise suitable. Suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and the technical-grade mixtures thereof. Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate and the mixtures thereof. Examples of further suitable polyol esters are the mono-, di- and triesters of trimethylolpropane optionally reacted with 1 to 30 mol of ethylene oxide or pentaerythritol with lauric acid, coconut fatty acid, tallow fatty acid, palmitic acid, stearic acid, oleic acid, behenic acid and the like. Preference is also given to trimethylpropane EO/PO trioleate, a mixture obtainable by the reaction of trimethylolpropane trioleate with ethylene oxide and propylene oxide under alkaline conditions. Ethylene oxide units (EO) and propylene oxide units (PO) are incorporated, at least in part, into the ester groups of the trimethylolpropane trioleate. The trimethylpropane EO/PO trioleate is characterized by the statistical average of its content of EO and PO units per molecule. In one embodiment of the present invention, trimethylpropane EO/PO trioleate having 120 ethylene oxide units (EO) and 10 propylene oxide units (PO) is used.

Wax Bodies (Also Pearlizing Waxes)

Pearlizing waxes impart a shimmering white, pearly effect to the cosmetic preparations, which is particularly valued in hair shampoos and shower gels. Waxes without a pearlizing effect may however also be contained in the hair treatment compositions.

Suitable wax bodies are: alkylene glycol esters, fatty acid alkanolamides, partial glycerides, esters of polybasic, optionally hydroxy-substituted carboxylic acids, fatty alcohols, fatty ketones, fatty aldehydes, fatty ethers, fatty carbonates, ring-opening products of olefin epoxides and mixtures thereof.

The alkylene glycol esters are typically mono- and/or diesters of alkylene glycols having the formula (I), $$R^1CO(OA)_nOR^2 \qquad (I)$$

in which $R^1CO$ is a linear or branched, saturated or unsaturated acyl radical having 6 to 22 carbon atoms, $R^2$ is hydrogen or $R^1CO$ and A is a linear or branched alkylene radical having 2 to 4 carbon atoms and n is numbers from 1 to 5. Typical examples are mono- and/or diesters of ethylene glycol, propylene glycol, diethylene glycol, dipropylene glycol, triethylene glycol or tetraethylene glycol with fatty acids having 6 to 22, preferably 12 to 18 carbon atoms as: caproic acid, caprylic acid, 2-ethylhexanoic acid, capric acid, lauric acid, isotridecanoic acid, myristic acid, palmitic acid, palm oleic acid, stearic acid, isostearic acid, oleic acid, elaidic acid, petroselinic acid, linoleic acid, linolenic acid, elaeostearic acid, arachic acid, gadoleic acid, behenic acid and erucic acid and technical-grade mixtures thereof. Particular preference is given to the use of ethylene glycol monostearate and/or distearate.

Other wax bodies such as fatty acid alkanolamides, have the formula (II), $$R^3CO-NR^4-B-OH \tag{II}$$

in which $R^3CO$ is a linear or branched, saturated or unsaturated acyl radical having 6 to 22 carbon atoms, $R^4$ is hydrogen or an optionally hydroxy-substituted alkyl radical having 1 to 4 carbon atoms and B is a linear or branched alkylene group having 1 to 4 carbon atoms. Typical examples are condensation products of ethanolamine, methylethanolamine, diethanolamine, propanolamine, methylpropanolamine and dipropanolamine and mixtures thereof with caproic acid, caprylic acid, 2-ethylhexanoic acid, capric acid, lauric acid, isotridecanoic acid, myristic acid, palmitic acid, palm oleic acid, stearic acid, isostearic acid, oleic acid, elaidic acid, petroselinic acid, linoleic acid, linolenic acid, elaeostearic acid, arachic acid, gadoleic acid, behenic acid and erucic acid and technical-grade mixtures thereof. Particular preference is given to using stearic acid ethanolamide.

Partial glycerides are mono and/or diesters of glycerol with linear, saturated and/or partially unsaturated fatty acids, for example, caproic acid, caprylic acid, capric acid, lauric acid, myristic acid, palmitic acid, palm oleic acid, tallow fatty acid, stearic acid, behenic acid and technical-grade mixtures thereof. They have the formula (III), $$\begin{array}{l} CH_2O(CH_2CH_2O)_x-COR^5 \\ | \\ CH-O(CH_2CH_2O)_y R^6 \\ | \\ CH_2O(CH_2CH_2O)_z-R^7 \end{array} \tag{III}$$

in which $R^5CO$ is an acyl radical having 6 to 22 carbon atoms, preferably a linear, saturated acyl radical having 6 to 22 carbon atoms, $R^6$ and $R^7$ are each independently hydrogen or $R^5CO$, x, y and z in total are 0 or numbers from 1 to 30 and X is an alkali metal or alkaline earth metal, with the proviso that at least one of the two radicals $R^6$ and $R^7$ is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, tallow fatty acid monoglyceride, tallow fatty acid diglyceride, behenic acid monoglyceride, behenic acid diglyceride and technical-grade mixtures thereof which may still comprise minor amounts of triglyceride from the production process.

Also suitable as wax bodies as a preferred group are esters of polybasic, optionally hydroxy-substituted carboxylic acids with fatty alcohols having 6 to 22 carbon atoms. Suitable acid components of these esters are, for example, malonic acid, maleic acid, fumaric acid, adipic acid, sebacic acid, azelaic acid, dodecanedioic acid, phthalic acid, isophthalic acid and, in particular, succinic acid and also malic acid, citric acid and in particular tartaric acid and mixtures thereof. The fatty alcohols comprise 6 to 22, preferably 12 to 18 and especially 16 to 18 carbon atoms in the alkyl chain. Typical examples are caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenic alcohol, elaeostearyl alcohol, arachyl alcohol, gadoleyl alcohol, behenyl alcohol, erucyl alcohol and brassidyl alcohol and technical-grade mixtures thereof. The esters may be present as full or partial esters, preference being given to using monoesters and especially diesters of carboxylic acids or hydroxycarboxylic acids. Typical examples are succinic acid mono- and dilauryl esters, succinic acid mono- and dicetearyl esters, succinic acid mono- and distearyl esters, tartaric acid mono- and dilauryl esters, tartaric acid mono- and dicocoalkyl esters, tartaric acid mono- and dicetearyl esters, citric acid mono-, di- and trilauryl esters, citric acid mono-, di- and tricocoalkyl esters and citric acid mono-, di- and tricetearyl esters.

As a third preferred group of wax bodies, use may be made of fatty alcohols having the formula (IV), $$R^8OH \tag{IV}$$

in which $R^9$ is a linear, optionally hydroxy-substituted alkyl radical and/or acyl radical having 16 to 48, preferably 18 to 36 carbon atoms. Typical examples of suitable alcohols are cetearyl alcohol, hydroxystearyl alcohol, behenyl alcohol and oxidation products of long-chain paraffin.

Fatty ketones, which are suitable as components, preferably have the formula (V), $$R^9-CO-R^{10} \tag{V}$$

in which $R^9$ and $R^{10}$ are each independently alkyl and/or alkenyl radicals having 1 to 22 carbon atoms, with the proviso that they have in total at least 24 and preferably 32 to 48 carbon atoms. The ketones may be prepared by methods according to the prior art, for example by pyrolysis of the corresponding fatty acid magnesium salts. The ketones may be symmetrical or asymmetrical in structure; preferably, however, the two radicals $R^{13}$ and $R^{14}$ differ only by one carbon atom and are derived from fatty acids having 16 to 22 carbon atoms.

Fatty aldehydes suitable as wax bodies preferably correspond to the formula (VI), $$R^{11}COH \tag{VI}$$

in which $R^{11}CO$ is a linear or branched acyl radical having 24 to 48, preferably 28 to 32 carbon atoms.

Likewise, suitable fatty ethers are preferably of the formula (VII), $$R^{12}-O-R^{13} \tag{VII}$$

in which $R^{12}$ and $R^{13}$ are each independently alkyl and/or alkenyl radicals having 1 to 22 carbon atoms, with the proviso that they have in total at least 24 and preferably 32 to 48 carbon atoms. Fatty ethers of the type mentioned are typically prepared by acidic condensation of the corresponding fatty alcohols. Fatty ethers with particularly advantageous pearlescent properties are obtained by condensation of fatty alcohols having 16 to 22 carbon atoms such as cetyl alcohol, cetearyl alcohol, stearyl alcohol, isostearyl alcohol, oleyl alcohol, behenyl alcohol and/or erucyl alcohol.

Suitable components are, furthermore, fatty carbonates, preferably of the formula (VIII), $$R^{14}O-CO-OR^{15} \tag{VIII}$$

in which $R^{14}$ and $R^{15}$ are each independently alkyl and/or alkenyl radicals having 1 to 22 carbon atoms, with the proviso that they have in total at least 24 and preferably 32 to 48 carbon atoms. The substances are obtained by transesterifying, for example, dimethyl carbonate or diethyl carbonate with the corresponding fatty alcohols in a manner known per se. Accordingly, the fatty carbonates may be symmetrical or asymmetrical in structure. However, preference is given to using carbonates in which $R^{14}$ and $R^{15}$ are identical and are alkyl radicals having 16 to 22 carbon atoms. Particular preference is given to transesterification products of dimethyl carbonate or diethyl carbonate with cetyl alcohol, cetearyl alcohol, stearyl alcohol, isostearyl alcohol, oleyl alcohol, behenyl alcohol and/or erucyl alcohol in the form of their mono- and diesters or technical-grade mixtures thereof.

Epoxide ring-opening products are known substances which are customarily prepared by acid-catalyzed reaction of terminal or internal olefin epoxides with aliphatic alcohols. The reaction products preferably have the formula (IX),

in which R16 and R17 are hydrogen or an alkyl radical having 10 to 20 carbon atoms, with the proviso that the sum total of carbon atoms of R16 and R17 is in the range of 10 to 20 and R18 is an alkyl and/or alkenyl radical having 12 to 22 carbon atoms and/or is the radical of a polyol having 2 to 15 carbon atoms and 2 to 10 hydroxyl groups. Typical examples are ring-opening products of α-dodecene epoxide, α-hexadecene epoxide, α-octadecene epoxide, α-eicosene epoxide, α-docosene epoxide, i-dodecene epoxide, i-hexadecene epoxide, i-octadecene epoxide, i-eicosene epoxide and/or i-docosene epoxide with lauryl alcohol, coconut fatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Preference is given to using ring-opening products of hexadecene and/or octadecene epoxides with fatty alcohols having 16 to 18 carbon atoms. If polyols are used for the ring opening in place of fatty alcohols, they are, for example, the following substances: glycerol; alkylene glycols such as ethylene glycol, diethylene glycol, propylene glycol, butylene glycol, hexylene glycol and polyethylene glycols having an average molecular weight of 100 to 1000 Daltons; technical-grade oligoglycerol mixtures having a degree of self-condensation of 1.5 to 10 such as technical-grade diglycerol mixtures having a diglycerol content of 40 to 50% by weight; methyol compounds such as, in particular, trimethylolethane, trimethylolpropane, trimethylolbutane, pentaerythritol and dipentaerythritol; lower alkyl glucosides particularly those having 1 to 8 carbon atoms in the alkyl radical such as methyl glucoside and butyl glucoside; sugar alcohols having 5 to 12 carbon atoms such as sorbitol or mannitol, sugars having 5 to 12 carbon atoms such as glucose or sucrose; amino sugars such as glucamine.

Consistency Regulators and Thickeners

Suitable consistency regulators are primarily fatty alcohols or hydroxy fatty alcohols having 12 to 22 and preferably 16 to 18 carbon atoms and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are for example aerosil grades (hydrophilic silicas), polysaccharides, especially xanthan gum, guar gum, agar agar, alginates and tyloses, carboxymethylcellulose, hydroxyethylcellulose and hydroxypropylcellulose, further higher molecular-weight polyethylene glycol monoesters and diesters of fatty acids, polyacrylates (e.g Carbopols® and pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS-5PC (Rheox) which are a mixture of cyclopentasiloxane, disteardimonium hectorite and propylene carbonate have also proved to be particularly effective. Surfactants such as, for example, ethoxylated fatty acid glycerides, esters of fatty acids with polyols, such as, for example, pentaerythritol or trimethylolpropane, fatty alcohol ethoxylates with a narrowed homolog distribution or alkyl oligoglucosides, and electrolytes, such as sodium chloride and ammonium chloride, are also suitable.

Superfatting Agents

Use may be made, as superfatting agents, of substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers.

Stabilizers

Stabilizers which can be used are metal salts of fatty acids, such as, for example, magnesium, aluminum and/or zinc stearate or ricinoleate.

Polymers

The presence of at least one cationic polymer is advantageous, preferably from the group of cationically modified cellulose derivatives, PQ 10, PQ 67, cationically modified guar derivatives, such as, for example, Dehyquart® Guar N, guar hydroxypropyltrimonium chloride, cationic homo- or copolymers based on acrylamide, cationic homo- or copolymers based on vinyl pyrrolidone, cationic homo- or copolymers based on quaternized vinyl imidazole and cationic homo- or copolymers based on methacrylates.

Suitable cationic polymers are, for example, quaternized hydroxyethylcellulose, also obtainable under the name Polymer JR 400® from Amerchol, cationic starch, copolymers of diallylammonium salts and acrylamides, quaternized vinylpyrrolidone/vinylimidazole polymers, such as Luviquat® (BASF), condensation products of polyglycols and amines, quaternized protein hydrolyzates, polypeptides and amino acids, for example lauryldimonium hydroxypropyl hydrolyzed collagen (Lamequat® L/Grünau), quaternized wheat polypeptides, polyethyleneimine, cationic silicone polymers such as, for example, amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides such as, for example, described in FR-A 2252840 and also the crosslinked water-soluble polymers thereof, cationic chitin derivatives such as quaternized chitosan, optionally in microcrystalline distribution, condensation products of dihaloalkylene, such as, for example, dibromobutane with bis-dialkylamines, such as, for example, bisdimethylamino-1,3-propane, cationic guar gum such as, for example, Jaguar® CBS, Jaguar® C-17, Jaguar® C-16 from Celanese, quaternized ammonium salt polymers such as, for example, Mirapol® A-15, Mirapol® AD-1, Mirapol® AZ-1 from Miranol. Especially suitable cationic polymers are polyquaternium-68, obtainable as Luviquat® Supreme AT 1, or polyquaternium-11, obtainable as Luviquat® PQ 11 AT 1.

The cationic polymers are present in the hair treatment compositions preferably in amounts of 0.02 to 5 wt %, preferably 0.05 to 3 wt % and particularly preferably in amounts of 0.1 to 2 wt %.

Useful anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers and optionally derivatized cellulose ethers and silicones.

Silicone Compounds

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which at room temperature may be either liquid or else in the form of a resin. Also suitable are simethicones, which are mixtures of dimethicones with an average chain length of from 200 to 300 dimethylsiloxane units and hydrogenated silicates.

UV Light Protection Filters

UV light protection factors are understood to mean, for example, organic substances (light protection filters) which are liquid or crystalline at room temperature and which are capable of absorbing ultraviolet rays and of re-releasing the energy absorbed in the form of radiation of longer wavelength, for example heat. UVB filters may be oil-soluble or water-soluble. Examples of oil-soluble substances are:
- 3-benzylidenecamphor or 3-benzylidenenorcamphor and derivatives thereof, e.g. 3-(4-methylbenzylidene)camphor;
- 4-aminobenzoic acid derivatives, preferably 2-ethylhexyl 4-(dimethylamino)benzoate, 2-octyl 4-(dimethylamino)benzoate and amyl 4-(dimethylamino)benzoate;
- esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di-2-ethylhexyl 4-methoxybenzmalonate;
- triazine derivatives, such as, for example, 2,4,6-trianilino-(p-carbo-2'-ethyl-1'-hexyloxy)-1,3,5-triazine and octyltriazone or dioctylbutamidotriazone (Uvasorb® HEB);
- propane-1,3-diones, for example 1-(4-tert-butylphenyl)-3-(4'-methoxyphenyl)propane-1,3-dione;
- ketotricyclo(5.2.1.0)decane derivatives.

Suitable water-soluble substances are:
- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and its salts;
- sulfonic acid derivatives of 3-benzylidenecamphor, for example 4-(2-oxo-3-bornylidenemethyl)benzenesulfonic acid and 2-methyl-5-(2-oxo-3-bornylidene)sulfonic acid and salts thereof.

Suitable typical UVA filters are especially derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UVA and UVB filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Combinations of this type are advantageously combined with water-soluble filters, for example 2-phenylbenzimidazole-5-sulfonic acid and the alkali metal, alkaline earth metal, ammonium, alkylammonium, alkanolammonium and glucammonium salts thereof.

In addition to the soluble substances mentioned, insoluble light protection pigments, specifically finely dispersed metal oxides and salts, are also useful for this purpose. Examples of suitable metal oxides are especially zinc oxide and titanium dioxide, and additionally oxides of iron, of zirconium, of silicon, of manganese, of aluminum and of cerium, and mixtures thereof. The salts used may be silicates (talc), barium sulfate or zinc stearate. The oxides and salts are used in the form of the pigments for skincare and skin-protecting emulsions and decorative cosmetics. The particles should here have an average diameter of less than 100 nm, preferably between 5 and 50 nm and in particular between 15 and 30 nm. They may have a spherical shape, but it is also possible to use those particles which have an ellipsoidal shape or a shape which deviates in some other way from the spherical configuration. The pigments may also be present in surface-treated form, i.e. hydrophilized or hydrophobized. Typical examples are coated titanium dioxides, such as, for example, titanium dioxide T 805 (Degussa) or Eusolex® T2000 (Merck). Suitable hydrophobic coatings are in particular silicones and specifically trialkoxyoctylsilanes or simethicones. In sunscreen compositions, preference is given to using micropigments or nanopigments. Preference is given to using micronized zinc oxide.

Biogenic Active Ingredients and Antioxidants

Biogenic active ingredients are understood to mean, for example, tocopherol, tocopherol acetate, tocopherol palmitate, ascorbic acid, (deoxy)ribonucleic acid and the fragmentation products thereof, β-glucans, retinol, bisabolol, allantoin, phytantriol, panthenol, AHA acids, amino acids, ceramides, pseudoceramides, essential oils, plant extracts, such as, for example, *Prunus* extract, bambara nut extract or vitamin complexes.

Antioxidants interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), also (metal) chelating agents (e.g. α-hydroxy fatty acids, palmitic acid, phytic acid, lactoferrin), α-hydroxy acids (e.g. citric acid, lactic acid, malic acid), humic acid, gallic acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids), suitable in accordance with the invention, of these specified active ingredients.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

Antidandruff Active Ingredients

Suitable antidandruff active ingredients include piroctone olamine (1-hydroxy-4-methyl-6-(2,4,4-trimythylpentyl)-2-(1H)-pyridinonemonoethanolamine salt), Baypival® (climbazole), Ketoconazole®, (4-acetyl-1-{-4-[2-(2,4-dichlorophenyl)r-2-(1H-imidazol-1-ylmethyl)-1,3-dioxylan-c-4-ylmethoxyphenyl}piperazine, ketoconazole, Elubiol, selenium disulfide, colloidal sulfur, sulfur polyethylene glycol sorbitan monooleate, sulfur ricinol polyethoxylate, sulfur tar distillates, salicylic acid (and/or in combination with hexachlorophene), undecylenic acid monoethanolamide sulfosuccinate sodium salt, Lamepon® UD (protein-undecylenic acid condensate), zinc pyrithione, aluminum pyrithione and magnesium pyrithione/dipyrithione-magnesium sulfate.

Further Additives

Swelling agents for aqueous phases which may be used are montmorillonites, clay mineral substances, pemulen and alkyl-modified Carbopol grades (Goodrich). Further suitable polymers and swelling agents can be found in the overview by R. Lochhead in Cosm. Toil. 108, 95 (1993). Suitable insect repellents are N,N-diethyl-m-toluamide, 1,2-pentanediol or ethyl butylacetylaminopropionates, and a suitable self-tanning agent is dihydroxyacetone. Possible tyrosine inhibitors, which prevent the formation of melanin and are applied in depigmenting compositions, are, for example, arbutin, ferulic acid, kojic acid, coumaric acid and ascorbic acid (vitamin C).

Protein Hydrolysates

If desired, further protein hydrolyzates known from the prior art may be used, for example based on keratin such as the commercially available Nutrilan® Keratin W PP, or based on wheat, such as Gluadin® WLM Benz, Gluadin® WK or Gluadin® WP. It is also possible to add small amounts of free amino acids such as lysine or arginine.

Hydrotropes

Use may furthermore be made, in order to improve the flow behavior, of hydrotropes, such as, for example, ethanol, isopropyl alcohol or polyols. Polyols which are suitable here preferably have 2 to 15 carbon atoms and at least two hydroxyl groups. The polyols may comprise still other functional groups, in particular amino groups, or be modified with nitrogen. Typical examples are glycerol;

alkylene glycols, such as, for example, ethylene glycol, diethylene glycol, propylene glycol, butylene glycol, hexylene glycol, and polyethylene glycols with an average molecular weight of from 100 to 1,000 Daltons;

technical-grade oligoglycerol mixtures with a degree of self-condensation of from 1.5 to 10, such as, for example, technical-grade diglycerol mixtures with a diglycerol content of from 40 to 50 wt %;

methylol compounds, such as especially trimethylolethane, trimethylolpropane, trimethylolbutane, pentaerythritol and dipentaerythritol;

lower alkyl glucosides, especially those with 1 to 8 carbon atoms in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

amino sugars, such as, for example, glucamine;

dialcoholamines such as diethanolamine or 2-amino-1,3-propanediol.

Preservatives

Examples of suitable preservatives are benzoates, phenoxyethanol, formaldehyde solution, parabens, pentanediol or sorbic acid, levulinic acid or arachidonic acid, and also the silver complexes known under the designation Surfacine®, and the additional substance classes listed in Annex 6, parts A and B, of the Cosmetics Directive.

Perfume Oils and Aromas

Mention may be made, as perfume oils, of mixtures of natural and synthetic fragrances. Natural fragrances are extracts from flowers (lily, lavender, rose, jasmine, neroli, ylang ylang), stems and leaves (geranium, patchouli, petitgrain), fruits (aniseed, coriander, caraway, juniper), fruit peels (bergamot, lemon, orange), roots (mace, *angelica*, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tertbutylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethol, citronellol, eugenol, isoeugenol, geraniol, linalool, phenylethyl alcohol and terpineol, and the hydrocarbons include primarily the terpenes and balsams. However, preference is given to using mixtures of different fragrances which together produce a pleasant scent note. Essential oils of relatively low volatility, which are mostly used as aroma components, are also suitable as perfume oils, e.g. sage oil, chamomile oil, clove oil, melissa oil, mint oil, cinnamon leaf oil, linden blossom oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix coeur, iso-E-super, Fixolide NP, evernyl, iraldein gamma, phenylacetic acid, geranyl acetate, benzyl acetate, rose oxide, romillat, irotyl and floramat alone or in mixtures. Examples of suitable aromas include peppermint oil, spearmint oil, aniseed oil, star anise oil, cumin oil, *eucalyptus* oil, fennel oil, lemon oil, wintergreen oil, clove oil, menthol and the like.

Dyes

Dyes which can be used are the substances approved and suitable for cosmetic purposes, as listed, for example, in the publication "Kosmetische Färbemittel" [Cosmetic Colorants] from the Farbstoffkommission der Deutschen Forschungsgemeinschaft [Dyes commission of the German research society], Verlag Chemie, Weinheim, 1984, pp. 81-106. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). As a luminescent dye, it is also possible for luminol to be present. These dyes are usually used in concentrations of from 0.001 to 0.1% by weight, based on the total mixture.

Cosmetic Compositions

In the context of the present invention, particular preference is given to cosmetic hair treatment compositions which additionally comprise, aside from the inventive protein hydrolyzates, cationic polymers or cationic or pseudo-cationic surfactants.

According to one embodiment, the cosmetic composition for conditioning hair treatment comprises, aside from the inventive protein hydrolyzates, cationic polymers of the type described above, and also optionally additional emulsifiers, hydrotropes or further customary ingredients, with water being present to make up to 100 wt %. Conditioning hair compositions in the form of a serum preferably have compositions of this type.

According to a further embodiment, the cosmetic composition for conditioning hair treatment (also referred to as hair treatment composition) comprises, in combination with the inventive protein hydrolyzates,
cationic surfactants
waxes, preferably glyceride esters and/or fatty alcohol, and
water, and also
optionally at least one cationic polymer and/or
optionally nonionic surfactants.

Within this embodiment of the conditioning hair treatment compositions preferably
0.002 to 0.4 wt %, based on active substance content, of inventive protein hydrolyzate 0.1 to 15 wt % of cationic surfactants,
0.5 to 15 wt % of a wax, preferably triglyceride ester and/or fatty alcohol, and
0.0 to 5 wt % of at least one cationic polymer and/or
0.0 to 15 wt % of nonionic surfactants are present, wherein optionally further customary ingredients may be present, and water being present to make up to 100 wt %.

A further subject of the present invention relates to cosmetic compositions for cleansing skin and/or hair, wherein they comprise the inventive protein hydrolyzates and also additionally comprise anionic surfactants and amphoteric or zwitterionic surfactants.

This should be understood to include all cosmetic cleansing compositions intended for cleansing and caring for the skin, preferably shower gels, body washes, shower oils, foam baths or hand sanitizing lotions.

According to this embodiment, the cosmetic composition additionally comprises, in combination with the inventive protein hydrolyzates, anionic surfactants, amphoteric or zwitterionic surfactants and also optionally nonionic surfactants, optionally a cationic polymer and/or optionally pearlizing wax, with further customary ingredients optionally being able to be present and water being present to make up to 100 wt %.

Within this embodiment, preferably
0.002 to 0.4 wt %, based on active substance content, of inventive protein hydrolyzate 8 to 15 wt % of anionic surfactants,
0.5 to 5 wt % of amphoteric or zwitterionic surfactants,
0.0 to 5 wt % of at least one cationic polymer,
0.0 to 3 wt % of nonionic surfactants, and
0.0 to 2 wt % of pearlizing waxes, and also optionally further ingredients customary in skin treatment compositions, are present, water being present to make up to 100 wt %.

Examples of suitable combinations of the cosmetic compositions are given in the following examples section.

EXAMPLES

A) Preparation Examples of the Inventive Protein Hydrolyzates

Inventive Example 1

5 g of rice protein were suspended in 100 g of water. 15 g of soy protein were added thereto and the pH was adjusted to pH 8.5 using sodium hydroxide solution. 300 mg of protease (from *Bacillus Stilistirr*; Alcalase® from Novozymes) were subsequently added to the protein mixture and the mixture was stirred for 2 hours.

Inventive Example 2

The mixture obtained according to example 1 was adjusted to pH 7 and subsequently 300 mg of exopeptidase (from *Aspergillus oryzae*; e.g. Flavourzyme® from Novozymes) were added thereto and the mixture was stirred for a further 4 hours.

The mixtures obtained according to example 1 or 2 were worked up before being used. To this end, they had undissolved protein fragments removed from them using centrifugation or filtration, they were concentrated, and were adjusted to pH 4.2 for stabilization. The active substance content of the protein solution used in water was 20 wt %.

The mixture obtained according to inventive example 2, which had undissolved protein fragments removed therefrom using centrifugation, has the following amino acid composition:

Composition of Amino Acids in Wt %:

| Amino acids | Example 2 |
|---|---|
| Alanine | 4.48 |
| Arginine | 8.44 |
| Aspartic acid | 11.83 |
| Cysteine/cystine | 1.54 |
| Glutamic acid | 19.67 |
| Glycine | 4.27 |
| Histidine | 2.61 |
| Isoleucine | 4.29 |
| Leucine | 7.38 |
| Lysine | 6.17 |
| Methionine | 1.11 |
| Phenylalanine | 4.94 |
| Proline | 5.03 |
| Serine | 5.48 |
| Threonine | 3.93 |
| Tyrosine | 3.88 |
| Valine | 4.95 |

Comparative Examples

Comparative Example 1: Soy Hydrolyzate (not According to the Invention)

Example 1 was repeated, but only with soy protein and without rice protein.

Amino acid composition: 7.8% arginine, 6.2% lysine

Comparative Example 2: Rice Hydrolyzate (not According to the Invention)

Example 1 was repeated, but only with rice protein and without soy protein.

Amino acid composition: 8.1% arginine, 4.4% lysine

Comparative Example 3: Keratin Hydrolyzate (not According to the Invention)

100 g of water were initially charged, and adjusted with a base to ~pH 9.4. Subsequently, 3.75 g of keratin wool were stirred in and, by addition of hydrogen peroxide $H_2O_2$, the oxidative pretreatment of the wool was started (duration: ~10 hours). Subsequently, 0.10 g of a protease (e.g. from *Bacillus licheniformis*; Alcalase from Novozymes), was added. After complete hydrolysis, the remaining water-insoluble wool residues were separated off using filtration and the resulting product was adjusted to pH 4.2 for stabilization.

Amino acid composition: 9.3% arginine, 2.5% lysine

Comparative Example 4: Wheat Hydrolyzate (not According to the Invention)

Example 1 was repeated, but only with wheat protein.
Amino acid composition: 3.1% arginine, 1.4% lysine B) Use Examples B1) Hair Repair Using DSC (Differential Scanning Calorimetry) Method The DSC method is a common thermal analysis method for measuring amounts of absorbed/emitted heat of a sample on heating. Because of the different heat flows between sample and reference during the temperature change program (heating rate), conclusions can be drawn on the denaturation temperatures of the treated hair (sample) relative to untreated hair (reference). The apparatus DSC TA Instruments Q 100 with Autosampler was used. The measurement was carried out according to the method of F. J. Wortmann et al., from: J. Cosmet. Sci., 53, 219-228 (July/August 2002); in a deviation from this, measurement was carried out with a heating rate of 2° C./min.

As sample, Caucasian hair that had been ultra-bleached three times, treated with a 5 wt % aqueous solution of the soy/rice hydrolyzate obtained according to inventive example 2, was tested. 5 wt % aqueous solutions of comparative examples 1 to 4 served as benchmark:

Results:

| | DSC in ° C. |
|---|---|
| Inventive | 5.68 ± 0.20 |
| Comparative 1 (keratin) | 3.73 ± 0.10 |
| Comparative 2 (wheat) | 4.06 ± 0.14 |
| Comparative 3 (soy) | 3.64 ± 0.10 |
| Comparative 4 (rice) | 4.26 ± 0.10 |

Damaged hair which was treated with the inventive protein hydrolyzate according to example 2 demonstrates a higher decomposition temperature, i.e. an improvement in the denaturation temperature of the hair, which is attributed to an improvement in the hair structure.

B2) Method for Determining Hair Breakage (Hair Breakage Test)

The resistance of the hair to mechanical stress was determined by what is referred to as the "hair breakage test". To this end, the hair tresses were treated with a conditioner comprising keratin hydrolyzate (composition, see below). After leaving to act for 3 minutes, rinsing was carried out for 1 minute and the process was repeated once. Subsequently, the hair tresses were placed on a grid and dried for 1 hour with a blowdryer. The hair tresses were then combed 50 000 times with a combing machine. The broken hair fragments were weighed and related to the weight of the hair tresses.

The following was tested in a conditioner of the following composition: the values are in wt %:

| | INCI | Placebo (without protein hydrolyzate) | Comparative example | Inventive example |
|---|---|---|---|---|
| Lanette ® O | Cetyl Stearyl Alcohol | 4.5 | 4.5 | 4.5 |
| Myritol ® 312 | Caprylic/Capric Triglyceride | 2 | 2 | 2 |
| Dehyquart ® A CA | Cetyl Trimethyl Ammonium Chloride | 2 | 2 | 2 |

| INCI | Placebo (without protein hydrolyzate) | Comparative example | Inventive example |
|---|---|---|---|
| Dehyquart ® F 75 | Distearoylethyl Hydroxy-ethylmonium Methosulfate (and) Cetearyl Alcohol | 1.4 | 1.4 | 1.4 |
| Comparative example 1 | | | 1 | |
| Example 2 | | | | 1 |
| Sodium benzoate | | 0.3 | 0.3 | 0.3 |
| Perfume | | 0.3 | 0.3 | 0.3 |
| Water | | 89.5 | 88.5 | 88.5 |

Statistical significance (p=0.05), calculated according to Tukey's HSD test.

Result:

| | Comparative eample 1 | Eample 2 |
|---|---|---|
| Hair breakage vs. placebo | No change | −20% |

The hair treated with the inventive protein hydrolyzate according to example 2 demonstrates 20% less hair breakage than the hair with placebo treatment and than the hair tresses treated with keratin hydrolyzate according to comparative example 1.

B3) Conditioner with Protein Hydrolyzate

A conditioner with the following composition was prepared (values in wt %):

| | INCI | Conditioner according to the invention |
|---|---|---|
| Cosmedia ® Triple C | Polyquaternium 37(and) Dicaprylylcarbonate (and) Lauryl Glucoside | 0.40 |
| Dehyquart ® F 75/ | Distearoylethyl Hydroxyethylmonium Methosulfate (and) Cetearyl Alcohol | 2.50 |
| Lanette ® O | Cetyl stearyl alcohol | 3.50 |
| Cutina ® HVG | Hydrogenated Vegetable Glycerides | 1.00 |
| Cetiol ® C 5 | Coco Caprylate | 2.00 |
| Cetiol ® SB 45 | *Butyrospermum Parkii* Butter | 0.70 |
| Lipofructyl ® Argan LS 9779 | *Argania Spinosa* Kernel Oil | 0.20 |
| Water | | 83.90 |
| Dehyquart ® A-CA | Cetyl Trimethyl Ammonium Chloride | 3.00 |
| Example 2 | | 2.00 |
| Perfume | | 0.30 |
| Sodium benzoate | | 0.50 |
| Citric acid | | q.s. |

B4) Leave-in Serum Conditioner

| | INCI | Inventive |
|---|---|---|
| Water | | 91.53 |
| Example 2 | | 2.00 |
| Melhydran ® LS 9876 | Aqua(and)Butylene Glycol(and)Mel Extract (and) Glycerin (and) Urea | 1.00 |
| D-Panthenol ® 75 W | Panthenol | 0.67 |
| Glycerol | Glycerol | 3.00 |
| Sodium benzoate | | 0.5 |
| Eumulgin ® CO 40 | PEG-40 Hydrogenated Castor Oil | 0.5 |
| Copherol ® 1250 C | Tocopheryl Acetate | 0.5 |

-continued

| | INCI | Inventive |
|---|---|---|
| Perfume | | 0.3 |
| Citric acid | | q.s |

B5) Application in Hair Shampoos

The following formulations were prepared. The values are in wt %.

| | | Shampoo 1 | |
|---|---|---|---|
| Ingredients | INCI | | % |
| Texapon ® N 70 | Sodium Laureth Sulfate | | 14.30 |
| Dehyton ® PK 45 | Cocamidopropylbetaine | | 5.40 |

-continued

| | | Shampoo 1 | |
|---|---|---|---|
| Ingredients | INCI | | % |
| Dehyquart ® Guar N | Guar Hydroxypropyltrimonium Chloride | | 0.20 |
| Lamesoft ® Care | PEG-4 Distearyl Ether (and) Sodium Laureth Sulfate (and) Distearyl Ether (and) Dicaprylyl Ether | | 3.00 |
| Dehydol ® LS 2 Deo N | Laureth-2 | | 1.00 |
| Water, demin. | Aqua | | 74.60 |
| Example 2 | | | 0.50 |
| Sodium Chloride | Sodium Chloride | | 0.50 |

Shampoo 1

| Ingredients | INCI | % |
| --- | --- | --- |
| Sodium Benzoate | Sodium Benzoate | 0.50 |
| Citric Acid | Citric Acid | qs |

Shampoo 2

| Ingredients | INCI | % |
| --- | --- | --- |
| Texapon ® N 70 | Sodium Laureth Sulfate | 14.30 |
| Dehyton ® PK 45 | Cocamidopropylbetaine | 5.40 |
| Water, demin. | Aqua | 77.30 |
| Example 2 | | 0.50 |
| Sodium Chloride | Sodium Chloride | 2.00 |
| Sodium Benzoate | Sodium Benzoate | 0.50 |
| Citric Acid | Citric Acid | qs |

Shampoo 3

| Ingredients | INCI | % |
| --- | --- | --- |
| Texapon ® N 70 | Sodium Laureth Sulfate | 14.30 |
| Dehyton ® PK 45 | Cocamidopropylbetaine | 5.40 |
| Dehyquart ® Guar N | Guar Hydroxypropyltrimonium Chloride | 0.20 |
| Water, demin. | Aqua | 76.70 |
| Example 2 | | 1.00 |
| Sodium Chloride | Sodium Chloride | 1.60 |
| Perfume Cotton Touch | Perfume | 0.30 |
| Sodium Benzoate | Sodium Benzoate | 0.50 |
| Citric Acid | Citric Acid | qs |

Comb tests on dry hair demonstrated a reduction in the required combability of 20% compared to the placebo shampoo without inventive protein hydrolyzate.

Shampoo 4 "Extra Care"

| Ingredients | INCI | % |
| --- | --- | --- |
| Water | Water | 68.12 |
| Dehyquart ® Guar N | Guar Hydroxypropyltrimonium Chloride | 0.20 |
| Dehyton ® PK 45 | Cocamidopropylbetaine | 2.70 |
| Luviquat ® UltraCare | Polyquaternium-44 | 1.15 |
| Texapon ® N 70 | Sodium Laureth Sulfate | 12.90 |
| Plantapon ® LC 7 | Laureth-7 Citrate | 1.00 |
| Plantacare ® 818 UP | Coco-Glucoside | 0.40 |
| Lamesoft ® PO 65 | Coco-Glucoside, Glyceryl Oleate | 5.00 |
| Cetiol ® LDO | Dicaprylyl Ether, Lauryl Alcohol | 0.70 |
| Example 2 | | 2.00 |
| D-Panthenol 75 W | Panthenol | 1.33 |
| Euperlan ® PK 710 Benz | Glycol Distearate, Sodium Laureth Sulfate, Cocamide MEA | 3.00 |
| Sodium Benzoate | Sodium Benzoate | 0.50 |
| Perfume | Perfume | qs |
| Magnesium Chloride Hexahydrate | Magnesium Chloride | 1.00 |
| Citric Acid (50% solution) | Citric Acid | qs |
| Sodium Chloride | Sodium Chloride | qs |

Shampoo 5 "Thickening Shampoo"

| Ingredients | INCI | % |
| --- | --- | --- |
| Texapon ® N 70 | Sodium Laureth Sulfate | 14.30 |
| Dehyton ® PK 45 | Cocamidopropylbetaine | 5.40 |
| Plantapon ® LC 7 | Laureth-7 Citrate | 2.00 |
| Gluadin ® WQ PP | Laurdimonium Hydroxypropyl Hydrolyzed Wheat Protein | 0.50 |
| Example 2 | | 2.00 |
| D-Panthenol 75 W | Panthenol | 1.33 |
| Euperlan ® PK 710 Benz | Glycol Distearate, Sodium Laureth Sulfate, Cocamide MEA | 3.00 |
| Perfume | Perfume | qs |
| Water | Water | 68.97 |
| Sodium Benzoate | Sodium Benzoate | 0.50 |
| Magnesium Chloride Hexahydrate | Magnesium Chloride | 1.00 |
| Dehydol LS 2 Deo N | Laureth-2 | 1.00 |
| Citric Acid (50% solution) | Citric Acid | qs |
| Sodium Chloride | Sodium Chloride | qs |

B6) Conditioner as Gel

Conditioning Gel

| Ingredients | INCI | % |
| --- | --- | --- |
| Water, demin. | Aqua | 80.90 |
| Example 2 | | 1.50 |
| Ethanol | Alcohol | 15.00 |
| Dehyquart ® Guar HP | Guar Hydroxypropyltrimonium Chloride | 1.50 |
| Citric Acid | Citric Acid | 0.30 |
| Luviquat ® Supreme AT 1 | Polyquaternium-68 | 2.00 |
| Perfume Cotton Touch | Perfume | 0.30 |

B7) Styling Mousse

| Ingredients | INCI | % |
| --- | --- | --- |
| Water, demin. | Aqua | 82.70 |
| Example 2 | | 2.00 |
| Luviquat ® Supreme AT 1 | Polyquaternium-68 | 7.50 |
| Luviquat ® PQ 11 AT 1 | Polyquaternium-11 | 7.50 |
| Cremophor ® A 25 | Ceteareth-25 | 0.50 |
| Perfume Cotton Touch | Perfume | 0.10 |
| Sodium Benzoate | Sodium Benzoate | 0.30 |
| Citric Acid (20% solution) | Citric Acid | 1.40 |

B8) Conditioner for Natural Cosmetics

| Ingredients | INCI | % |
| --- | --- | --- |
| Plantaquat ® NC | Cetearyl Alcohol (and) Lecithin (and) Sodium Cetearyl Sulfate (and) Olus Oil [EU] | 9.0 |
| Lanette ® O | Cetearyl Alcohol | 2.0 |
| Cetiol ® C5 | Coco-Caprylate | 2.0 |
| Cegesoft ® SB | *Butyspermum Parkii* Butter | 2.0 |
| Example 2 | | 2.0 |
| Sodium Benzoate | Sodium Benzoate | 0.5 |
| Perfume | Perfume | q.s. |
| Water | Water | add 100 |

B9) Hair and Body Wash

| Hair and Body Wash -Cleansing composition 1 for natural cosmetics | | |
|---|---|---|
| Ingredients | INCI | % |
| Water, demin. | Water | 68.20 |
| Sulfopon ® 1216 G | Sodium Coco-Sulfate | 8.00 |
| Plantacare ® 818 UP | Coco-Glucoside | 13.30 |
| Euperlan ® GREEN | Lauryl Glucoside (and) Stearyl Citrate | 2.00 |
| Lamesoft ® PO 65 | Coco-Glucoside (and) Glyceryl Oleate | 2.00 |
| Example 2 | | 0.50 |
| Sodium Benzoate | Sodium Benzoate | 0.50 |
| Perfume | Perfume | q.s. |
| Apple juice 100%, direct juice | *Pyrus Malus* (Apple) Juice | 3.00 |
| Citric Acid (50%) | Citric Acid | 1.20 |
| Sodium Chloride | Sodium Chloride | 1.30 |

| Hair and Body Wash -Cleansing composition 2 for natural cosmetics | | |
|---|---|---|
| Ingredients | INCI | % |
| Water, demin. | Water | 70.10 |
| Sulfopon ® 1216 G | Sodium Coco-Sulfate | 8.00 |
| Plantacare ® 818 UP | Coco-Glucoside | 13.30 |
| Lamesoft ® PO 65 | Coco-Glucoside (and) Glyceryl Oleate | 2.00 |
| Example 2 | | 0.50 |
| Sodium Benzoate | Sodium Benzoate | 0.50 |
| Perfume | Perfume | q.s. |
| Apple juice 100%, direct juice | *Pyrus Malus* (Apple) Juice | 3.00 |
| Citric Acid (50%) | Citric Acid | 1.20 |
| Sodium Chloride | Sodium Chloride | 1.30 |

The invention claimed is:

1. A protein hydrolyzate consisting of free and peptide-bound amino acids, wherein 8.0-25 wt % of the amino acids are arginine and 6.0-25 wt % of the amino acids are lysine.

2. The protein hydrolyzate according to claim 1, wherein 5.0 to 25 wt % of the amino acids are lysine.

3. The protein hydrolyzate according to claim 1, wherein 8.2 to 25% of the amino acids are arginine.

4. The protein hydrolyzate according to claim 1, wherein 8.2 to 8.5 wt % of the amino acids are arginine and 6.0 to 6.5 wt % of the amino acids are lysine.

5. A method for preparing a protein hydrolyzate according to claim 1, wherein a mixture of soy and rice proteins in a weight ratio of 2:1 to 4:1 is enzymatically hydrolyzed in the presence of at least one endopeptidase.

6. The method for preparing a protein hydrolyzate according to claim 5, wherein a mixture of soy and rice proteins in a weight ratio of 2:1 to 4:1 is enzymatically hydrolyzed in the presence of at least one endopeptidase and subsequently hydrolyzed once again in the presence of an exopeptidase.

7. A conditioner in a hair treatment composition, comprising the protein hydrolyzate of claim 1.

8. A method for improving the internal hair structure of hair, comprising treating the hair with the protein hydrolyzate of claim 1.

9. A cosmetic composition comprising the protein hydrolyzate according to claim 1, wherein the hydrolyzate is present in an amount of 0.002 to 0.4 wt % based on the active substance content.

10. A cosmetic composition for hair treatment comprising the protein hydrolyzates according to claim 1, wherein the composition additionally comprises cationic or pseudo-cationic surfactants or cationic polymers.

11. A cosmetic composition for cleansing skin and/or hair comprising the protein hydrolyzates according to claim 1, wherein the composition additionally comprises anionic surfactants and amphoteric or zwitterionic surfactants.

\* \* \* \* \*